(12) United States Patent
Ahn et al.

(10) Patent No.: US 8,052,108 B2
(45) Date of Patent: Nov. 8, 2011

(54) PROBE HOLDER

(75) Inventors: June Young Ahn, Seoul (KR); Ghi Young Kim, Anyang-si (KR)

(73) Assignee: Medison Co., Ltd., Kangwon-do (KR)

( * ) Notice: Subject to any disclaimer, the term of this patent is extended or adjusted under 35 U.S.C. 154(b) by 0 days.

(21) Appl. No.: 12/706,597

(22) Filed: Feb. 16, 2010

(65) Prior Publication Data

US 2010/0213322 A1   Aug. 26, 2010

(30) Foreign Application Priority Data

Feb. 16, 2009   (KR) .......................... 10-2009-0012385

(51) Int. Cl.
*A47F 5/00*   (2006.01)
(52) U.S. Cl. ...................... 248/309.1; 248/314; 248/918; 361/679.23
(58) Field of Classification Search .................. 248/201, 248/309.1, 311.2, 312, 685, 674, 310, 314, 248/315, 534, 918; 361/679.23; 220/737, 220/907
See application file for complete search history.

(56) References Cited

U.S. PATENT DOCUMENTS

| | | | | |
|---|---|---|---|---|
| 5,603,477 A | * | 2/1997 | Deutsch | 248/311.2 |
| 6,227,509 B1 | * | 5/2001 | Plocher et al. | 248/311.2 |
| 6,427,960 B1 | * | 8/2002 | Gehring et al. | 248/311.2 |
| 7,458,481 B2 | * | 12/2008 | Yuen | 220/737 |
| 7,559,520 B2 | * | 7/2009 | Quijano et al. | 248/309.1 |
| 2010/0025555 A1 | * | 2/2010 | Shigio et al. | 248/284.1 |

* cited by examiner

*Primary Examiner* — Terrell McKinnon
*Assistant Examiner* — Bradley Duckworth
(74) *Attorney, Agent, or Firm* — McDermott Will & Emery LLP (57) ABSTRACT

A probe holder includes a base and a holding part foldably provided to the base. The probe holder allows easy movement and maintenance of an ultrasonic diagnostic apparatus including the probe holder and to prevent the probe holder from being damaged by a wall or other objects and vice versa during movement of the ultrasonic diagnostic apparatus.

7 Claims, 10 Drawing Sheets

PROBE HOLDER

CROSS-REFERENCE TO RELATED APPLICATIONS

The present application claims priority from Korean Patent Application No. 10-2009-0012385 filed on Feb. 16, 2009, the entire subject matter of which is incorporated herein by reference.

BACKGROUND OF THE INVENTION

1. Field of the Invention

The present invention relates to a probe holder and, more particularly, to a probe holder for an ultrasonic diagnostic apparatus.

2. Description of the Related Art

Generally, an ultrasonic diagnostic apparatus refers to a non-invasive apparatus that irradiates an ultrasound signal from a surface of a patient body towards a target internal organ beneath the body surface and obtains an image of a monolayer or blood flow in soft tissue from information in the reflected ultrasound signal (ultrasound echo-signal). The ultrasonic diagnostic apparatus has been widely used for diagnosis of the heart, the abdomen, the urinary organs, and in obstetrics and gynecology due to various merits thereof such as small size, low price, real-time image display, and high stability through elimination of radiation exposure, as compared with other image diagnostic systems, such as X-ray diagnostic systems, computerized tomography scanners (CT scanners), magnetic resonance imagers (MRIs), nuclear medicine diagnostic apparatuses, and the like.

The ultrasonic diagnostic apparatus includes a cart-shaped main body for receiving main components thereof, a probe for transmitting and receiving ultrasound signals, a control panel having various switches and keys for inputting commands for manipulation of the apparatus, and a display unit for displaying an image of an ultrasonic diagnosis result.

When using the apparatus for ultrasound diagnosis of a target, an operator moves the probe with one hand while keeping the probe in contact with a surface of the target, and manipulates the control panel with the other hand. Then, the result of the ultrasound diagnosis is provided as an image through the display unit.

The ultrasonic diagnosis apparatus may further include a probe holder. A user hangs the probe on the probe holder when the probe is not in use, and removes the probe from the probe holder when using the probe. The probe holder generally protrudes from the main body or from an outer surface of the control panel.

In such an ultrasonic diagnostic apparatus, the probe holder protrudes from the apparatus to occupy a space thereon even when the probe is not received in the holder, thereby causing restrictions in movement and maintenance of the apparatus. Furthermore, the probe holder can collide with a wall or be caught by other objects during movement of the diagnostic apparatus, so that the probe holder can be damaged or can damage the wall or other things. Therefore, there is a need for an improved probe holder.

SUMMARY OF THE INVENTION

The present invention is conceived to solve the problems of the related art as described above, and an aspect of the present invention is to provide an improved probe holder configured to allow easy movement and maintenance of an ultrasonic diagnostic apparatus including the probe holder and to prevent the probe holder from being damaged by a wall or other objects or to prevent the wall or other objects from being damaged by the probe holder during movement of the ultrasonic diagnostic apparatus.

In accordance with one aspect of the invention, a probe holder includes a base and a holding part foldably provided to the base.

The holding part may be provided to the base to be rotatable about a single point.

The holding part may be rotated between a folded position where the holding part is folded to the base and a holding position where a probe is held in the probe holder.

The probe holder may further include an elastic member provided to the holding part to elastically bias the holding part to the holding position.

The holding part may be provided with a support interfering with the base such that the holding part is supported on the base via the support when unfolded.

The probe holder may further include a securing part securing the holding part to the base at the folded position.

The securing part may include a first securing member provided to the holding part and a second securing member provided to the base to secure the first securing member.

The holding part may include an upper holding member having an upper holding hole and provided to an upper side of the base and a lower holding member having a lower holding hole and provided to a lower side of the base.

The upper and lower holding members may be provided with an engaging part allowing the upper and lower holding members to be folded in an engaged state.

The engaging part may include an engaging member formed on the upper holding member to protrude into the upper holding hole and an engaging groove formed on the lower holding member to engage with the engaging member.

In accordance with another aspect of the invention, a probe holder includes a base; an upper holding member foldably provided to an upper side of the base; a lower holding member foldably provided to a lower side of the base; elastic members elastically biasing the upper and lower holding members to be folded; an engaging part provided to the upper and lower holding members to allow the lower holding member and the upper holding member to be folded in an engaged state; and a securing part comprising a first securing member provided to the upper holding member and a second securing member provided to the base to allow the upper and lower holding members to be selectively secured to the base.

BRIEF DESCRIPTION OF THE DRAWINGS

The above and other aspects, features and advantages of the invention will become apparent from the following description of exemplary embodiments given in conjunction with the accompanying drawings, in which.

DETAILED DESCRIPTION OF THE EMBODIMENT

Exemplary embodiments of the invention will now be described in detail with reference to the accompanying drawings. It should be noted that the drawings are not to precise scale and may be exaggerated in thickness of lines or size of components for descriptive convenience and clarity only. Furthermore, terms used herein are defined by taking functions of the invention into account and can be changed according to the custom or intention of users or operators. Therefore, definition of the terms should be made according to overall disclosures set forth herein.

Figure 1:
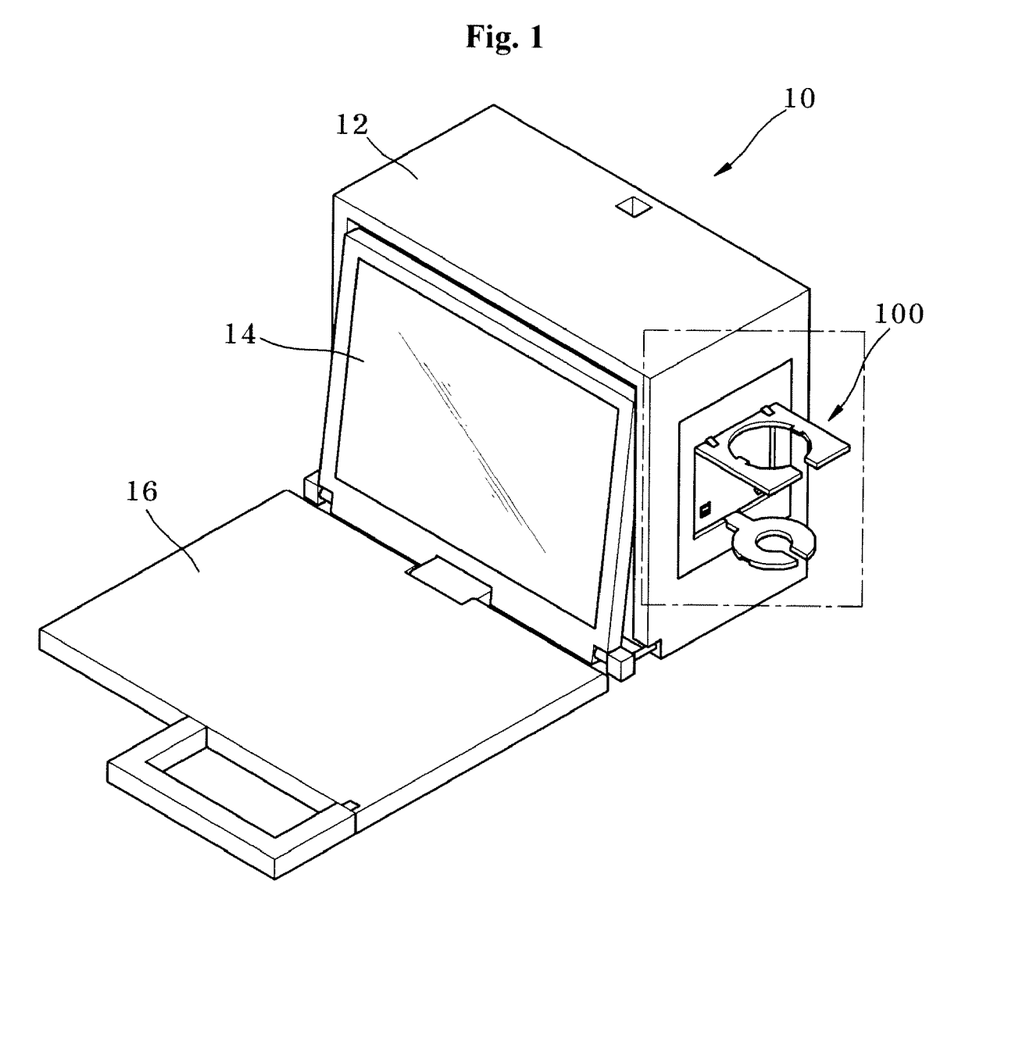
FIG. 1 is a perspective view of an ultrasonic diagnostic apparatus including a probe holder according to one embodiment of the present invention.

FIG. 1 is a perspective view of an ultrasonic diagnostic apparatus including a probe holder according to one embodiment of the invention.

Referring to FIG. 1, a probe holder 100 according to one embodiment of the invention is provided to an ultrasonic diagnostic apparatus 10. The ultrasonic diagnostic apparatus 10 includes a main body 12, a display unit 14, and a control panel 16.

The main body 12 defines an appearance of the apparatus 10 and includes various components for realizing functions of the apparatus 10. For example, the main body 12 includes a beam former (not show) that transmits ultrasound signals through a probe (not shown) and receives echo-ultrasound signals through the probe, a data formulator (not shown) that forms frame data based on signals output from the beam former, a processor (not shown) that forms a two-dimensional or three-dimensional image of a target based on the frame data, and a storage (not shown) that stores data.

The display unit 14 is movably provided to the main body 12. The display unit 14 is electrically connected to the main body 12 and displays data and images processed by the main body 12. The display unit 14 may be foldably provided to the main body 12.

The control panel 16 includes multiple manipulation keys (not shown) for operating the apparatus 10 or for selecting functions thereof and is connected to the main body 12. The control panel 16 is hingedly coupled to the display unit 14 to be foldable together with the display unit 14 with respect to the main body 12.

Figure 2:
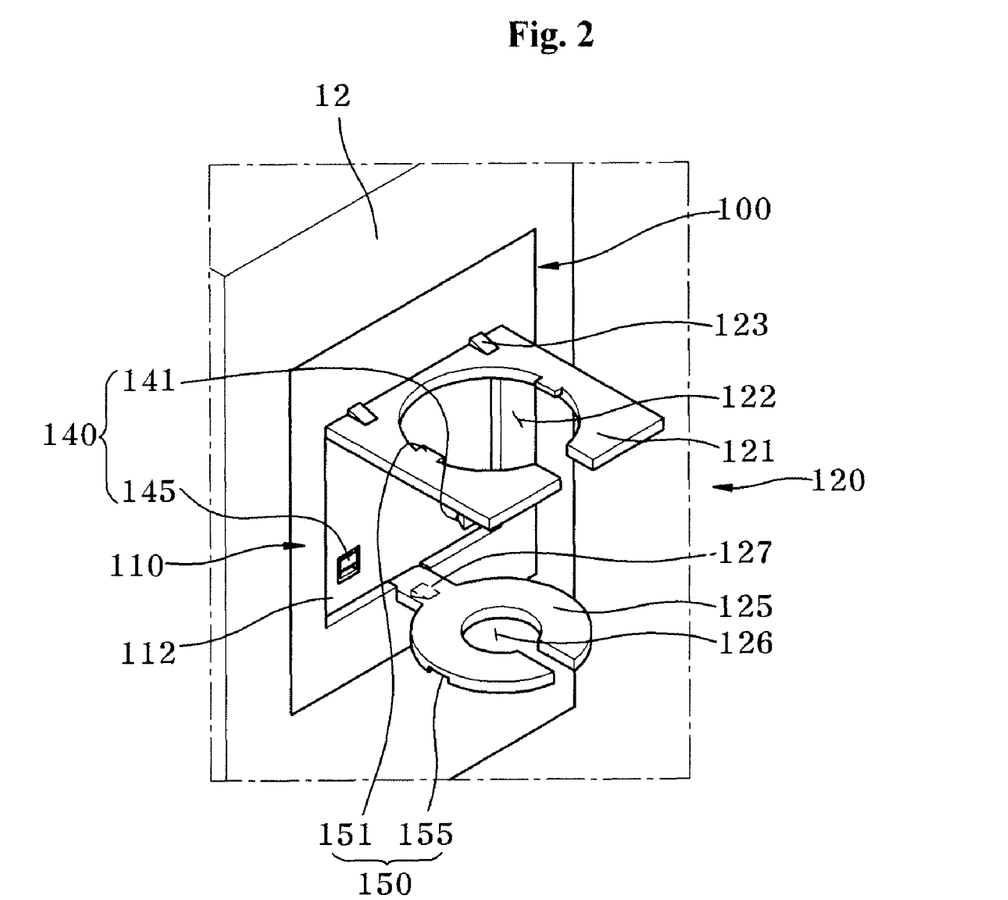
FIG. 2 is an enlarged perspective view of the probe holder of FIG. 1.
Figure 3:
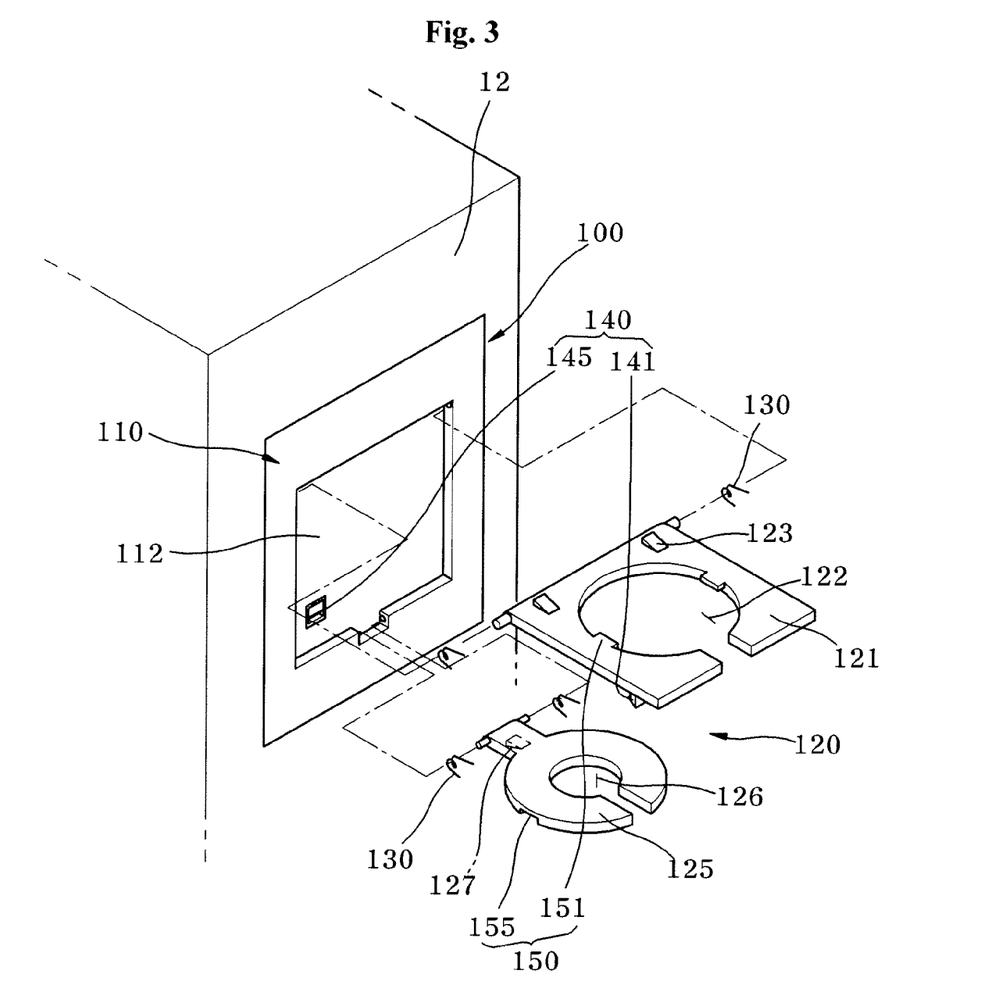
FIG. 3 is an exploded perspective view of the probe holder of FIG. 2.

FIG. 2 is an enlarged perspective view of the probe holder of FIG. 1 and FIG. 3 is an exploded perspective view of the probe holder of FIG. 2.

Referring to FIGS. 1 to 3, the probe holder 100 is provided to the main body 12. The probe holder 100 includes a base 110, a holding part 120, an elastic member 130, and a securing part 140.

The base 110 is provided to one side of the main body 12 to be exposed therefrom. The base 110 may be formed as a separate element with respect to the main body 12 and inserted into a groove on the main body 12. Alternatively, the base 110 may be integrally formed with the main body 12.

The base 110 is formed with an accommodation portion 112 therein. The accommodation portion 112 may be a depression formed into the base 110 to prevent the main body 12 from being exposed through the accommodation portion 112. Alternatively, the accommodation portion 112 may be a through-hole formed in the base 110 to expose the main body 12 through the accommodation portion 112. In this embodiment, the base 110 is provided as a separate element with respect to the main body 12 and the accommodation portion 112 is formed as the depression formed into the base 110.

The holding part 120 is foldably provided to the base 110. The holding part 120 includes an upper holding member 121 and a lower holding member 125.

The upper holding member 121 is foldably provided to an upper side of the base 110. The lower holding member 125 is foldably provided to a lower side of the base 110.

Each of the upper and lower holding members 121, 125 of the holding part 120 is provided to the base 110 to be rotatable about a "single point". Herein, the term "single point" may be the base 110 per se or may be a rotational shaft (reference numeral omitted) provided to each of the upper and lower holding members 121, 125. In this embodiment, each of the upper and lower holding members 121, 125 is provided to the base 110 to be rotatable about the rotational shaft.

The holding part 120 may be rotated between a folded position where the holding part 120 is folded to the base 110 and a holding position where a probe (not shown) is held in the probe holder. Here, the term "folded position" means a position where the holding part 120 is folded and does not protrude outside the base 110, and the term "holding position" means a position where the holding part 120 is unfolded to hold the probe.

According to this embodiment, the upper holding member 121 may be rotated upward from the folded position to the holding position, and the lower holding member 125 may be rotated downward from the folded position to the holding position. When rotated to the holding position, the upper and lower holding members 121, 125 are spaced from each other in the vertical direction.

In this embodiment, when the holding part 120 is located at a position where the upper and lower holding members 121, 125 of the holding part 120 are "accommodated" in the accommodation portion 112, the holding 120 is "located at the folded position." However, it should be noted that the invention is not limited to this configuration. According to an alternative embodiment, the holding part 120 "located at the folded position" may be located outside the base 110 instead of the accommodation portion 112. As such, the technical meaning of "located at the folded position" herein is not limited to "accommodation."

The upper holding member 121 is provided with an upper holding hole 122. The lower holding member 125 is provided with a lower holding hole 126. The upper holding hole 122 may be formed through the upper holding member 121 and the lower holding hole 126 may be formed through the lower holding member 125. When the upper and lower holding members 121, 125 are located at the holding positions, the probe can be held in the upper and lower holding holes 122, 126.

Namely, an upper section of the probe is held in the upper holding hole 122 and a lower section of the probe is held in the lower holding hole 126, so that two sections of the probe are supported by the holding part 120, thereby enabling the probe to be stably held in the holding part 120.

The upper holding member 121 has a shape corresponding to the accommodation part 112 to be accommodated in the accommodation part 112 at the folded position, and the lower holding member 125 has a shape corresponding to the upper holding hole 122 to be accommodated in the upper holding hole 122 at the folded position. Accordingly, the upper and lower holding members 121, 125 may be located coplanar with the outer surface of the main body 12 without protruding from the main body 12 when the holding part 120 is folded and located at the folded position.

In this embodiment, the accommodation part 112 and the upper holding member 121 have a rectangular shape, and the upper holding hole 122 and the lower holding member 125 have a circular shape. However, it should be understood that the invention is not limited thereto and various modifications can be made.

The holding part 120 may further include supports 123, 127. The supports 123, 127 are provided to the upper and lower holding members 121, 125, respectively, to interfere with the base 110 such that the holding part 120 can be supported on the base 110 via the supports 123, 127 when unfolded. Specifically, the supports 123, 127 protrude from one side of the upper holding member 121 adjacent to the base 110 and from one side of the lower holding member 125 adjacent to the base 110, respectively.

When the holding part 120 is unfolded, the supports 123, 127 interfere with the base 110 to support the upper and lower holding members 121, 125 such that the upper and lower holding members 121, 125 of the holding part 120 are secured at the holding positions thereof, respectively.

The elastic member 130 is provided to the holding part 120 to elastically bias the holding part 120 to the holding positions. Specifically, the elastic member 130 may be provided to each of the upper and lower holding members 121, 125 to elastically force the upper and lower holding members 121, 125 to be unfolded to the holding positions, respectively. The elastic members 130 may be torsion springs. The elastic members 130 may provide a pressing force to rotate the upper and lower holding members 121, 125.

The securing part 140 is provided to secure the holding part 120 to the base 110 at the folded position. The securing part 140 includes a first securing member 141 and a second securing member 145.

The first securing member 141 is provided to the holding part 120. Specifically, the first securing member 141 is provided to the upper holding member 121. The first securing member 141 protrudes from one side of the upper holding member 121 facing the accommodation part 112 of the base 110 towards the accommodation part 112 of the base 110 at the folded position.

The second securing member 145 is provided to the base 110. Specifically, the second securing member 145 is provided to the accommodation part 112 of the base 110 and disposed at a position corresponding to the position of the first securing member 141 when the holding part 120 is folded. The first securing member 141 is secured to the second securing member 145.

In this embodiment, the first securing member 141 is a hook and the second securing member 145 is a toggle type locking member into which the first securing member 141 is inserted.

According to this embodiment, when a user presses the upper holding member 121 to insert the first securing member 141 into the second securing member 145, the first securing member 141 is secured to the second securing member 145. When the user presses the upper holding member 121 again in this state, the first securing member 141 is released and separated from the second securing member 145. Such a locking manner and a detailed configuration embodying the locking manner are well known in the art, and a detailed description thereof will be omitted herein.

The first and second securing members 141, 145 allow the upper and lower holding members 121, 125 to be selectively secured to the base 110 at the folded positions. It should be understood that the first and second securing members 141, 145 can be embodied in various modifications.

According to the embodiment, the probe 100 may further include an engaging part 150. The engaging part 150 is provided to the upper and lower holding members 121, 125 to allow the upper and lower holding members 121, 125 to engage with each other at the folded positions. The engaging part 150 includes an engaging member 151 and an engaging groove 155.

The engaging member 151 is formed on the upper holding member 121 to protrude into the upper holding hole 122. The engaging groove 155 is formed on the lower holding member 125 to engage with the engaging member 151.

With this engaging part 150, the engaging member 151 engages with the engaging groove 155 when the holding part 120 is folded, so that the upper and lower holding members 121, 125 engage with each other. When the upper holding member 121 is secured to the base 110 by the securing part 140 at the folded position in this state, the lower holding member 125 engaging with the upper holding member 121 can also be secured to the base 110 at the folded position.

Accordingly, when the holding part 120 is located at the folded position, the upper and lower holding members 121, 125 may be coplanar with the outer surface of the main body 12 without protruding from the main body 12.

Figure 4:
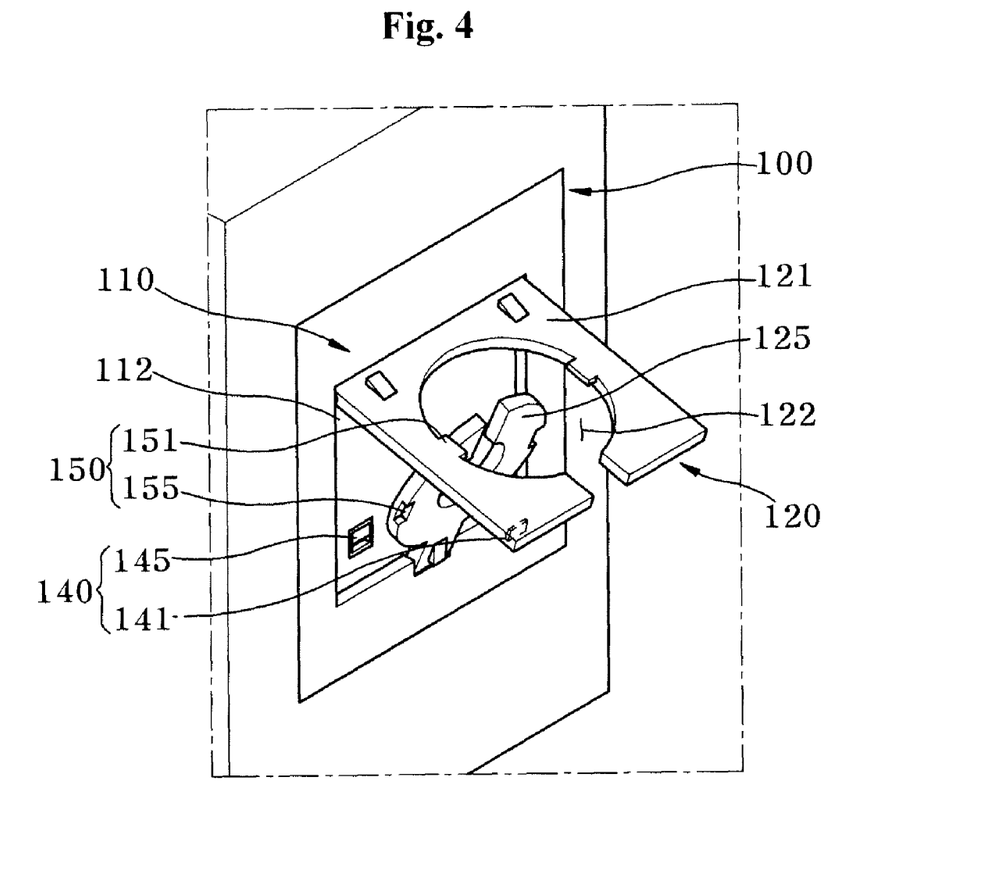
FIGS. 4 and 5 are perspective views of the probe holder of FIG. 2 in an unfolded state and a folded state, respectively.
Figure 5:
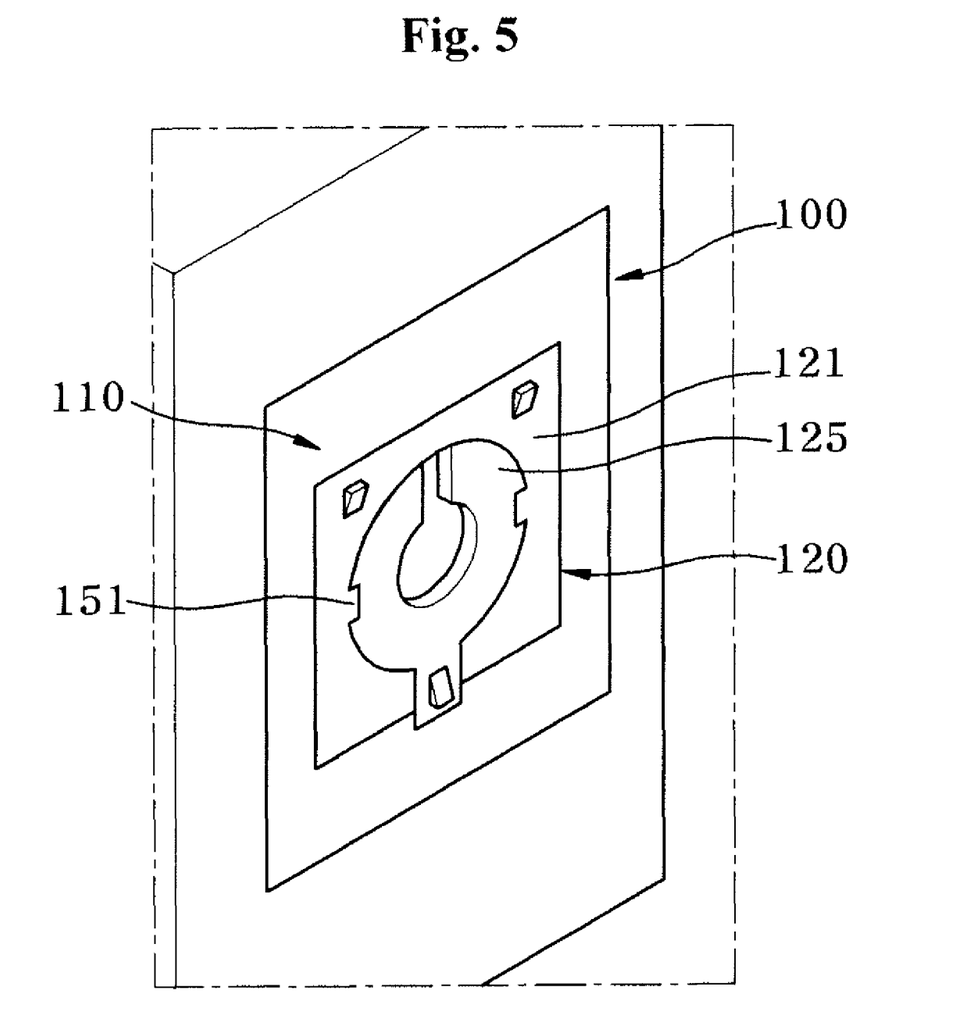
Figure 6:
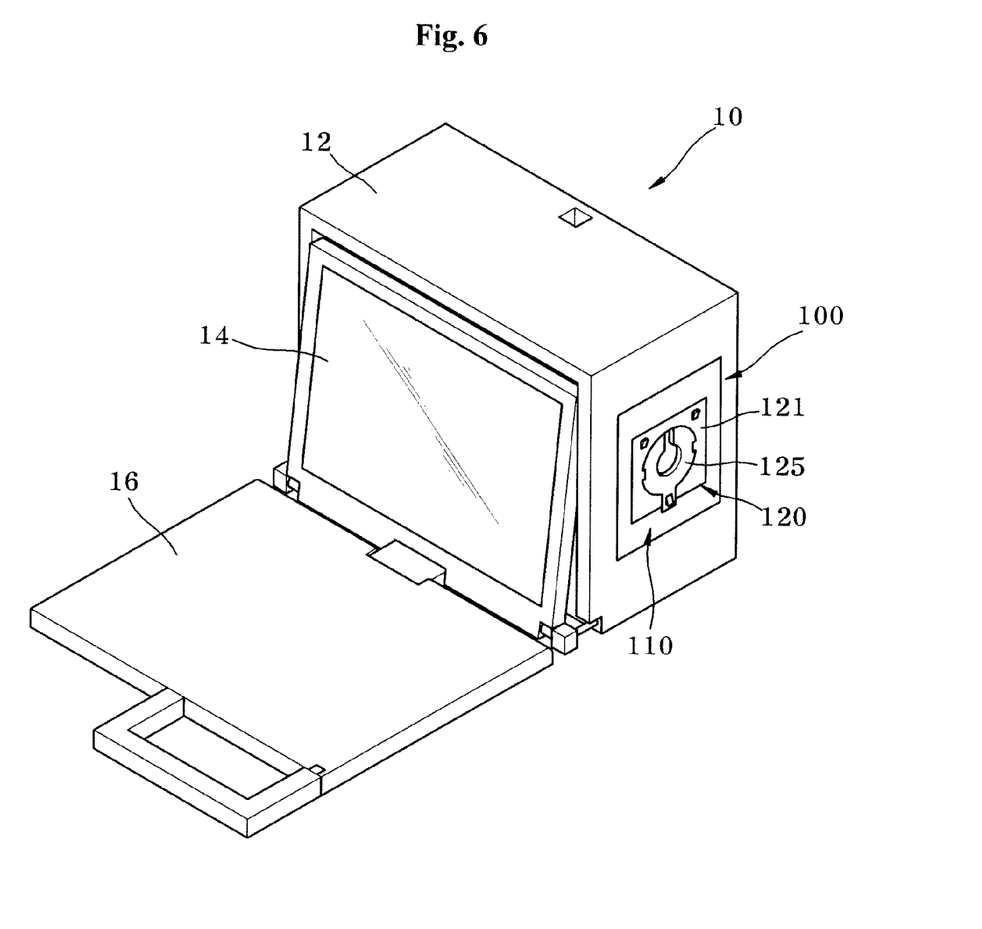
FIG. 6 is a perspective view of the ultrasonic diagnostic apparatus with the probe holder folded thereon.
Figure 7:
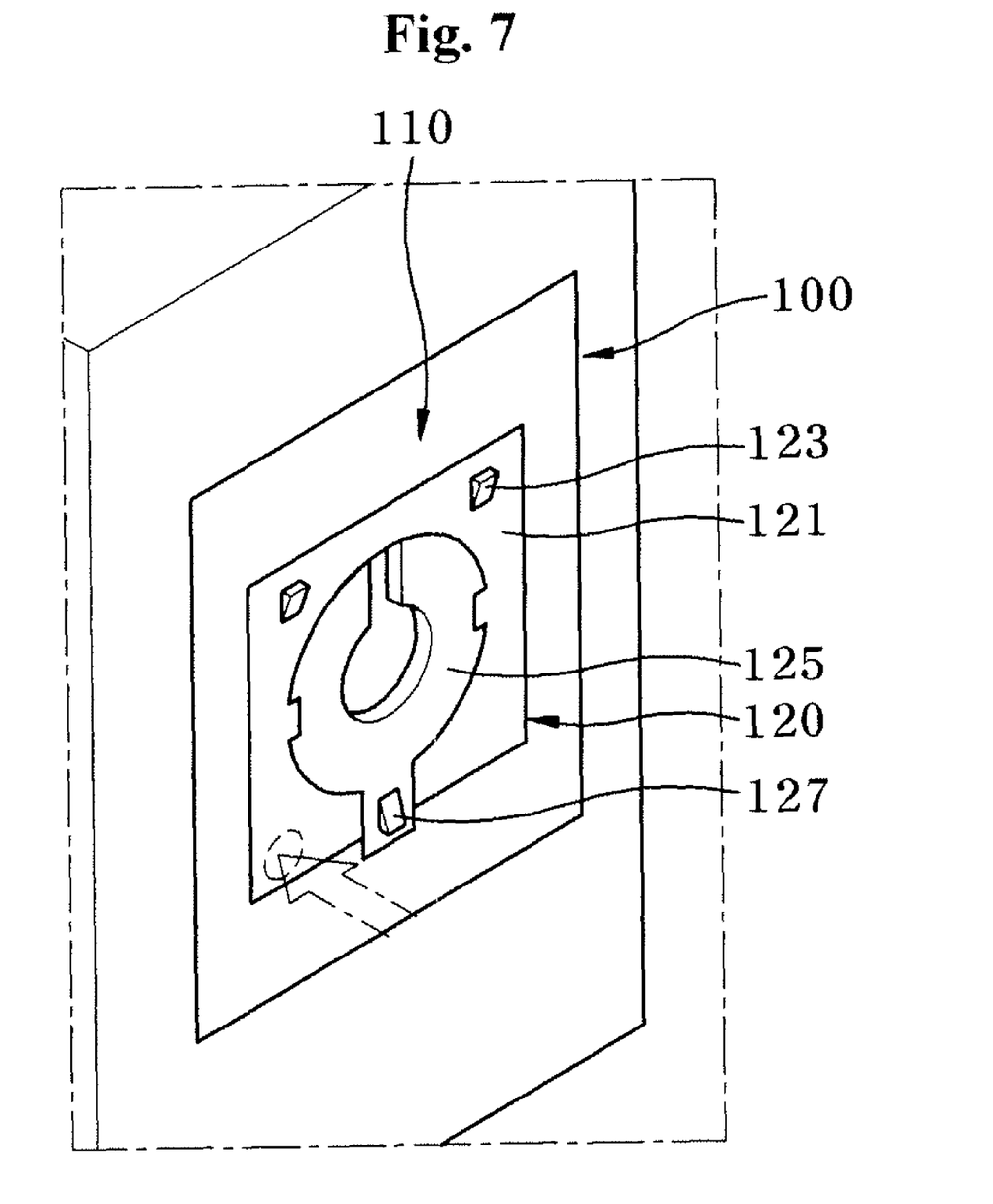
FIGS. 7 to 10 are perspective views of a process of unfolding the probe holder shown in FIG. 2.
Figure 8:
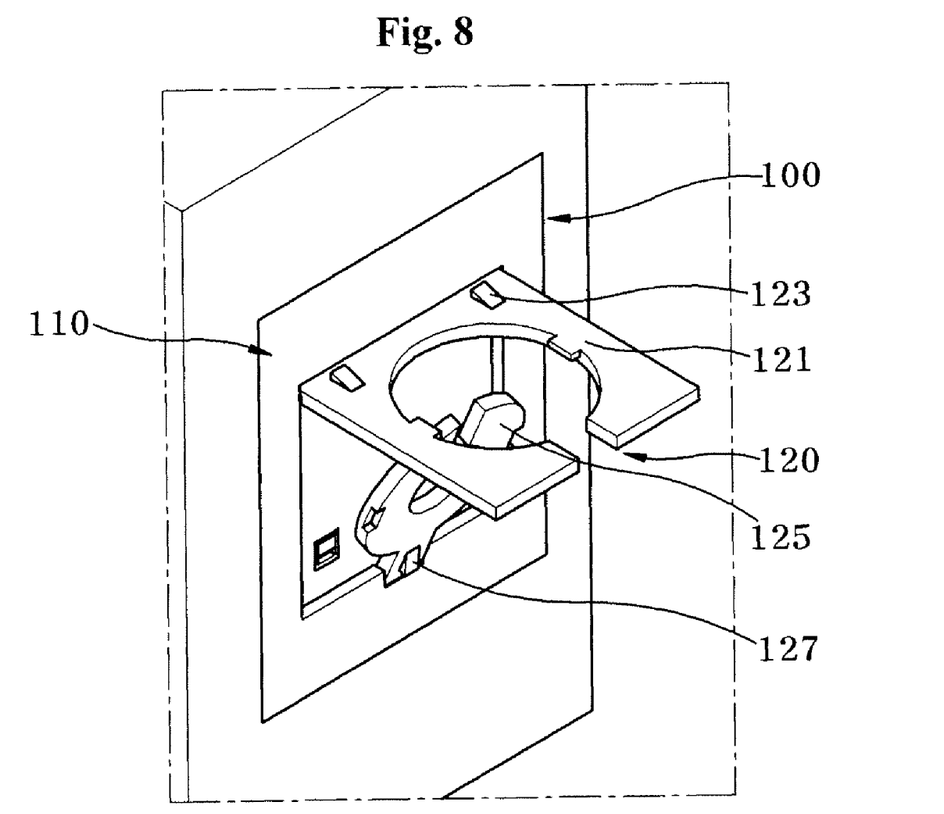
Figure 9:
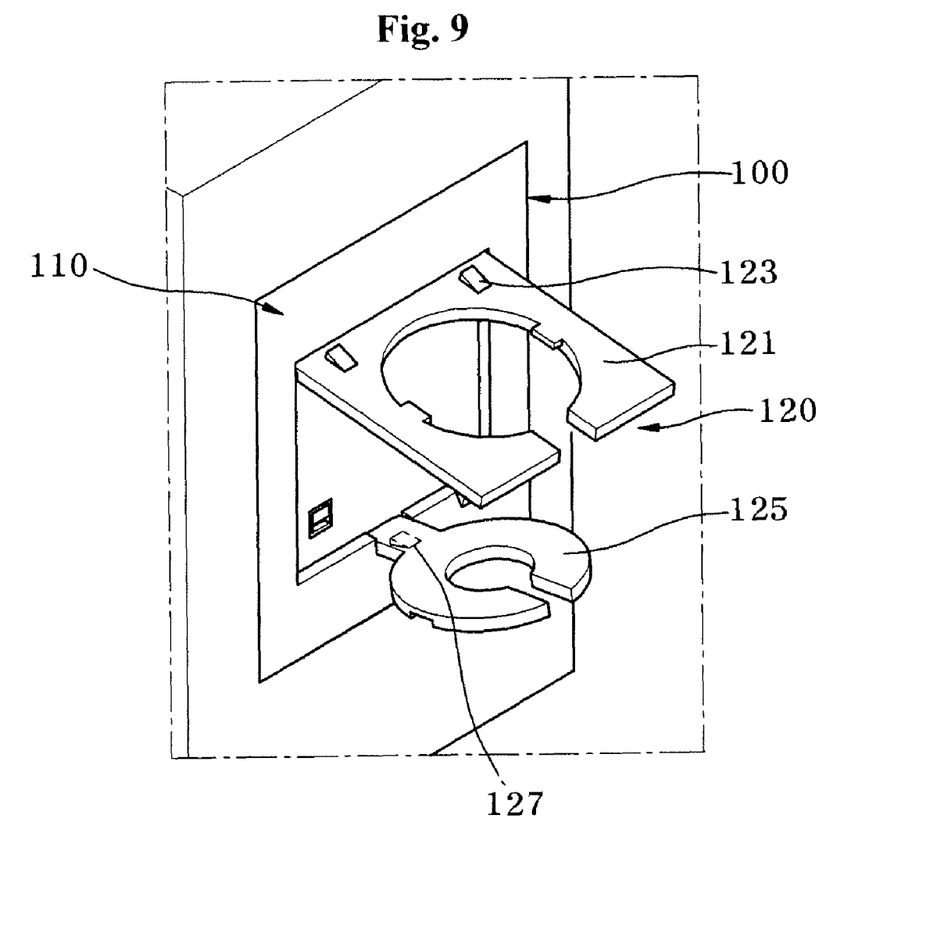

FIGS. 4 and 5 are perspective views of the probe holder of FIG. 2 in an unfolded state and a folded state, respectively, FIG. 6 is a perspective view of the ultrasonic diagnostic apparatus with the probe holder folded thereon, and FIGS. 7 to 10 are perspective views of a process of unfolding the probe holder shown in FIG. 2.

Next, operation of the probe holder according to this embodiment will be described with reference to FIGS. 2 to 10.

First, as shown in FIG. 2, when the holding part 120 is located at the holding position, a probe can be held in the holding part 120. In this case, the supports 123, 127 of the upper and lower holding members 121, 125 interfere with the base 110 such that the upper and lower holding members 121, 125 can be secured on the base 110 via the supports 123, 127 at the holding positions, respectively. Here, the upper and lower holding members 121, 125 secured at the holding positions may be unfolded perpendicular to the base 110 by the supports 123, 127.

When folding the holding part 120 in this state with the probe removed from the holding part 120, the upper and lower holding members 121, 125 are rotated from the holding positions towards the folded positions by pressing the upper and lower holding members 121, 125, as shown in FIG. 4. The lower holding member 125 may be rotated to reach the folded position earlier than the upper holding member 121.

As shown in FIG. 5, when rotation of the upper and lower holding members 121, 125 is completed, the upper and lower holding members 121, 125 are located at the folded positions, respectively. Here, the upper holding member 121 is secured to the base 110 at the folded position by coupling between the first securing member 141 (see FIG. 4) and the second securing member 145 (see FIG. 4), and the lower holding member 125 is secured to the base 110 when caught by the upper holding member 121 and accommodated in the upper holding hole 122 (see FIG. 4) at the folded position through engagement between the engaging member 151 and the engaging groove 155 (see FIG. 4).

As a result, the upper and lower holding members 121, 125 of the holding part 120 can be located coplanar with the outer surface of the main body 12, as shown in FIG. 6, so that the probe holder 100 does not protrude from the ultrasonic diagnosis apparatus 10.

To unfold the holding part 120 to the holding position in this state, the upper holding member 121 is pushed. In this case, a portion of the upper holding member 121 to which the securing part 140 (see FIG. 4) is located may be pushed. When the upper holding member 121 is pushed, coupling between the first securing member 141 (see FIG. 4) and the second securing member 145 (see FIG. 4) is released, thereby allowing the upper and lower holding members 121, 125 to be rotated to the holding positions by a force of the elastic members 130 (see FIG. 3), respectively.

In this case, the upper holding member 121 may be rotated to reach the holding position earlier than the lower holding member 125. For this purpose, the elastic member 130 for the upper holding member 121 may provide a stronger pressing force than the elastic member 130 for the lower holding member 125.

As such, when the upper holding member 121 is rotated to reach the holding position earlier than the lower holding member 125, interference between the upper and lower holding members 121, 125 can be prevented to ensure smooth rotation of the upper and lower holding members 121, 125.

Figure 10:
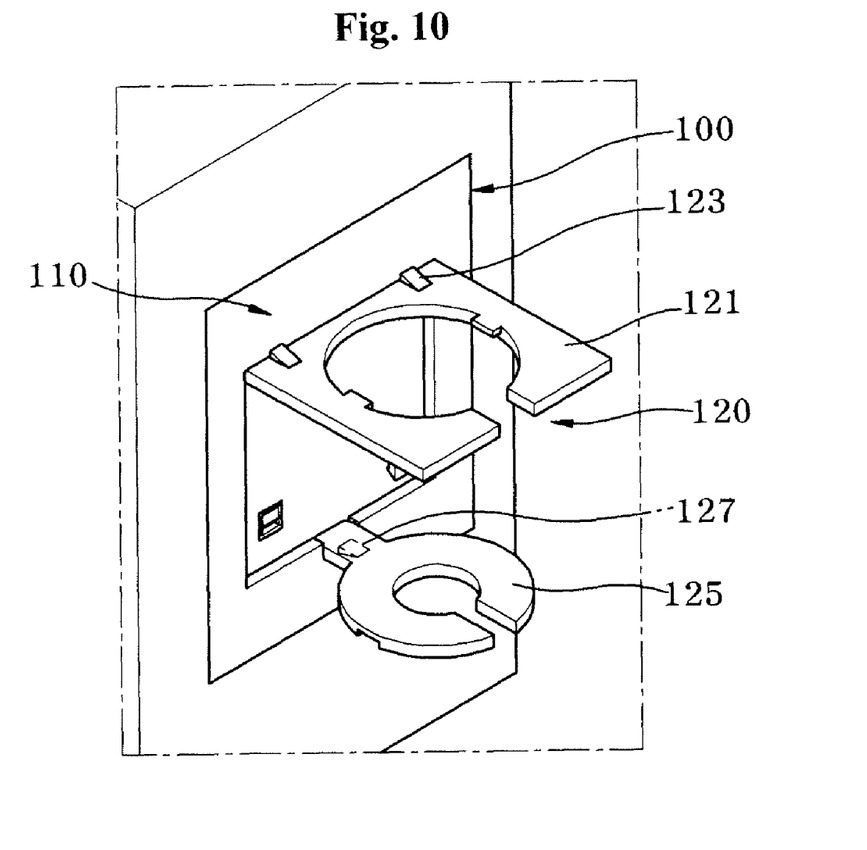

As shown in FIG. 10, when rotation of the upper and lower holding members 121, 125 is completed, the upper and lower holding members 121, 125 are located at the holding positions, respectively. Here, the supports 123, 127 of the upper and lower holding members 121, 125 interfere with the base 110, so that the upper and lower holding members 121, 125 are secured to the base 110 via the supports 123, 127 at the holding positions, respectively.

Here, the upper and lower holding members 121, 125 located at the holding positions may be fixedly unfolded perpendicular to the base 110 by the supports 123, 127, so that the probe can be held in the holding part 120 at the holding position.

As such, according to the embodiment of the invention, the probe holder includes the holding part that can be folded, as needed, to reduce the volume of the ultrasonic diagnostic apparatus, thereby allowing easy movement and maintenance of the apparatus while preventing the probe holder from being damaged by a wall or other objects and vice versa during movement of the apparatus.

Further, according to the embodiment of the invention, the folded probe holder does not protrude from the main body of the apparatus and can be folded to be coplanar with the outer surface of the main body, thereby allowing more easy movement and maintenance of the apparatus while providing a pleasing appearance thereto.

In understanding the scope of the invention, the terms "part" or "member" when used in the singular can have the dual meaning of a singular part or a plurality of parts unless otherwise stated. Further, the use of articles "a," "an" and "the" in the context of describing the invention, especially in the context of the embodiments, are to be construed to cover both the singular and the plural unless otherwise indicated herein or clearly contradicted by context.

Although some embodiments have been provided to illustrate the invention in conjunction with the drawings, it will be apparent to those skilled in the art that the embodiments are given by way of illustration only, and that various modifications and equivalent embodiments can be made without departing from the spirit and scope of the invention. Accordingly, the scope of the invention should be limited only by the accompanying claims.

What is claimed:

1. A probe holder equipped at a main body of an ultrasonic diagnostic apparatus, the probe holder comprising:
    a base provided to the main body and having an accommodation portion therein;
    a holding part foldably provided to the base, the holding part including an upper holding member and a lower holding member; and
    a securing part securing the holding part to the base at a folded position,
    wherein the upper holding member is foldably provided to the upper side of the base and includes an upper holding hole configured to hold an upper section of an ultrasound probe,
    wherein the lower holding member is foldably provided to the lower side of the base and includes a lower holding hole configured to hold a lower section of the ultrasound probe,
    wherein the upper holding member and the lower holding member are rotated between a folded position where the upper holding member and the lower holding member are folded to the base and a holding position where the ultrasound probe is held in the upper holding member and the lower holding member,
    wherein the holding part is provided with a support interfering with the base such that the holding part is supported on the base via the support when unfolded,
    wherein the lower holding member is accommodated in the upper holding hole of the upper holding member at the folded position.

2. The probe holder according to claim 1, further comprising;
    an elastic member provided to the holding part to elastically bias the holding part to the holding position.

3. The probe holder according to claim 1, wherein the securing part comprises a first securing member provided to the holding part and a second securing member provided to the base to secure the first securing member.

4. The probe holder according to claim 1, wherein the upper and lower holding members are provided with an engaging part allowing the upper and lower holding members to be folded in an engaged state.

5. The probe according to claim 4, wherein the engaging part comprises:
    an engaging member formed on the upper holding member to protrude into the upper holding hole; and
    an engaging groove formed on the lower holding member to engage with the engaging member.

6. A probe holder equipped at a main body of an ultrasonic diagnostic apparatus, the probe holder comprising;
    a base provided to the main body and having an accommodation portion therein;
    an upper holding member foldably provided to an upper side of the base, the upper holding member including an upper holding hole configured to hold an upper section of an ultrasound probe;
    a lower holding member foldably provided to a lower side of the base;
    elastic members elastically biasing the upper and lower holding members to be folded;
    an engaging part provided to the upper and lower holding members to allow the lower holding member to be folded to the upper holding member in an engaged state; and
    a securing part comprising a first securing member provided to the upper holding member and a second securing member provided to the base to allow the upper and lower holding members to be selectively secured to the base
    wherein the lower holding member is accommodated in the upper holding hole of the upper holding member at the engaged state.

7. The probe holder according to claim 1, wherein the accommodation portion is a depression formed in the base for accommodating the holding part.

* * * * *